United States Patent [19]
Paul et al.

[11] Patent Number: 5,770,570
[45] Date of Patent: Jun. 23, 1998

[54] METHOD OF DELIVERING A VASOACTIVE INTESTINAL POLYPEPTIDE, AN ENCAPSULATED VASOACTIVE INTESTINAL POLYPEPTIDE, AND A METHOD OF MAKING THE ENCAPSULATED VASOACTIVE INTESTINAL POLYPEPTIDE

[76] Inventors: Sudhir Paul, 6827 S. 145 St., Omaha, Nebr. 68137; Yasuko Noda, 4016 Emile St., Apartment 11, Omaha, Nebr. 68105; Israel Rubinstein, 2999 Lexington St., Highland Park, Ill. 60035

[21] Appl. No.: 519,180

[22] Filed: Aug. 25, 1995

Related U.S. Application Data

[63] Continuation of Ser. No. 224,488, Apr. 7, 1994, abandoned.
[51] Int. Cl.$^6$ .......................... A61K 9/127; A61K 38/17; A61K 38/22; A61K 38/25
[52] U.S. Cl. .............................. 514/12; 424/450; 514/21
[58] Field of Search ....................... 514/12, 21; 424/450

[56] References Cited

U.S. PATENT DOCUMENTS 4,745,100  5/1988  Gilbard et al. ............................. 514/12
5,264,618  11/1993  Felgner et al. ............................ 560/224

OTHER PUBLICATIONS

Epand et al., (1985), *Biophys. Chem.*, 23:39–48.
Gao et al., (1994), *Life Sciences*, 54:PL247–252.
Inooka et al., (1992), *Int. J. Peptide Protein Res.*, 40:456–464.
Kimura et al., (1992), *Int. J. Peptide Protein Res.*, 39:431–442.
Kloosterman et al., (1993), *Peptide Research*, 6:211–218.
Krstenansky et al., (1988), *Int. J. Peptide Protein Res.* 32:468–475.
Noda et al., (1994), *Biochimica et Biophysica Acta*, 1191:324–330.
Pasta et al., (1988), *Biochimica et Biophysica Acta*, 953:314–320.
Robinson et al., (1982), *Biopolymers*, 21:1217–1228.
Suzuki et al., (1995), *Life Sciences*, 57:1451–1457.
Suzuki et al., (1996), *Am. J. Physiol.*, 271:H282–H287.
Wu et al., (1982), *Biochemistry*, 21:4556–4562.
Katakai et al. Experimental Evidence for Predicted Transmembrane . . . Biopolymers. 1990, vol. 30, pp. 815–819.
Kondo et al. Conformation and the Properties of Porcine Brain . . . Polymer Journal. 1987, vol. 19, No. 12, pp. 1359–1364.
Noda et al, FASEB J. vol. 7, (Mar. 28, 1993 –Apr. 1, 1993) p. A182.
Gao et al, Life Sciences vol. 54 p. PL247 (Mar. 1994).
Stallwood, J. Biol. Chem. vol. 267 p. 19617 (1992).
Musso et al Biochem. vol. 27 p. 8174 (1988).

*Primary Examiner*—Jeffrey E. Russel
*Attorney, Agent, or Firm*—Cushman Darby & Cushman IP Group of Pillsbury Madison & Sutro LLP

[57] ABSTRACT

Provided is a method for delivering a vasoactive intestinal polypeptide (VIP) liposome product to a target tissue of a mammal. The VIP is expressed on and in a liposome. Also provided is a method of preparing the VIP liposome product comprising cholesterol, phosphatidyl choline, and phosphatidyl glycerol.

20 Claims, 8 Drawing Sheets

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Leu Lys Lys Leu Leu Lys Leu
    1                         5

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO:3:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

His Ala Asp Ala Ile Phe Thr Ser Ser Tyr Arg Arg Ile Leu Gly Gln
1               5                   10                  15

Leu Tyr Ala Arg Lys Leu Leu His Glu Ile Met Asn Arg Gln Gln Gly
            20                  25                  30

Glu Arg Asn Gln Glu Gln Arg Ser Arg Phe Asn
            35                  40

(2) INFORMATION FOR SEQ ID NO:4:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40

(2) INFORMATION FOR SEQ ID NO:5:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

His Ala Asp Gly Val Phe Thr Ser Ser Tyr Arg Arg Ile Leu Gly Gln
1               5                   10                  15

Leu Ser Ala Lys Lys Tyr Leu Glu Ser Leu Met
            20                  25

(2) INFORMATION FOR SEQ ID NO:6:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:6:

His Ser Asp Gly Thr Phe Thr Ser Glu Leu Ser Arg Leu Arg Asp Ser
1               5                   10                  15

Ala Arg Leu Gln Arg Leu Leu Gln Gly Leu Val
                20              25

( 2 ) INFORMATION FOR SEQ ID NO:7:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:7:

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
                20              25

( 2 ) INFORMATION FOR SEQ ID NO:8:

( i ) SEQUENCE CHARACTERISTICS:
      ( A ) LENGTH: 38 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:8:

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
                20              25                  30

Gln Arg Val Lys Asn Lys
                35

( 2 ) INFORMATION FOR SEQ ID NO:9:

( i ) SEQUENCE CHARACTERISTICS:
      ( A ) LENGTH: 38 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:9:

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
                20              25                  30

Pro Arg Pro Pro Ser Ser
                35

( 2 ) INFORMATION FOR SEQ ID NO:10:

( i ) SEQUENCE CHARACTERISTICS:
      ( A ) LENGTH: 35 amino acids
      ( B ) TYPE: amino acid
      ( C ) STRANDEDNESS: single
      ( D ) TOPOLOGY: linear (  i i ) MOLECULE TYPE: peptide ( x i ) SEQUENCE DESCRIPTION: SEQ ID NO:10:

His Ser Asp Ala Ile Phe Thr Gln Gln Tyr Ser Lys Leu Leu Ala Lys
1               5                   10                  15

Leu Ala Leu Gln Lys Tyr Leu Ala Ser Ile Leu Gly Ser Arg Thr Ser
            20              25              30

Pro Pro Pro
        35

( 2 ) INFORMATION FOR SEQ ID NO:11:

( i ) SEQUENCE CHARACTERISTICS:
     ( A ) LENGTH: 26 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:11:

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20              25

( 2 ) INFORMATION FOR SEQ ID NO:12:

( i ) SEQUENCE CHARACTERISTICS:
     ( A ) LENGTH: 29 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:12:

His Ser Asp Ala Val Phe Thr Asp Asn Tyr Thr Arg Leu Leu Arg Lys
1               5                   10                  15

Gln Met Ala Val Lys Lys Tyr Leu Asn Ser Ile Leu Asn
            20              25

( 2 ) INFORMATION FOR SEQ ID NO:13:

( i ) SEQUENCE CHARACTERISTICS:
     ( A ) LENGTH: 4 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:13:

Pro Phe Arg Xaa
1

METHOD OF DELIVERING A VASOACTIVE INTESTINAL POLYPEPTIDE, AN ENCAPSULATED VASOACTIVE INTESTINAL POLYPEPTIDE, AND A METHOD OF MAKING THE ENCAPSULATED VASOACTIVE INTESTINAL POLYPEPTIDE

This is a continuation of application Ser. No. 08/224,488, filed on Apr. 7, 1994, which was abandoned upon the filing hereof.

BACKGROUND OF THE INVENTION

1. Field of the Invention

The invention relates to a method of delivering a vasoactive intestinal polypeptide (hereinafter "VIP") to a target tissue, a VIP liposome product where VIP is expressed on and in liposomes, and a method of making the VIP liposome product having increased biological potency and decreased side effects.

2. Background of Related Art

VIP is a 28-amino acid neuropeptide which is known to display a broad profile of biological actions and to activate multiple signal transducing pathways. See, Said, S. I. (1984) *Peptides* 5, (Suppl. 1) 149–150, and Paul, S. and Ebadi, M. (1993) *Neurochem. Int.* 23, 197–214.

A Schiffer-Edmundson projection of VIP as a π-helix reveals segregation of apolar and polar residues onto the opposite faces of the helix and that this amphipathic character is also evident when VIP is modeled as a distorted α-helix, which is reported in Musso, G. F., Patthi, S., Ryskamp, T. C., Provow, S., Kaiser, E. T. and Velicelebi, G. (1988) *Biochemistry* 27, 8174–8181. A correlation between the helix-forming tendency of VIP analogues and their biological activity is described in Bodanszky, M., Bodanszky, A., Klausner, Y. S. and Said, S. I., (1974) *Bioorgan Chem.* 3, 133–140. In pure water, the spectral characteristics of VIP are consistent with those of a random coil. However, organic solvents and anionic lipids induce helix-information in the molecule. See, Robinson, R. M., Dlakeney, Jr., E. W. and Mattice, W. L. (1982) *Biopolymers* 21, 1217–1228; Hamed, M. M., Robinson, R. M. and Mattice, W. L. (1983) *Biopolymers* 22, 1003–1021; and Bodanszky, M. Bodanszyk, A., Klausner, Y. S. and said, S. I. (1974) *Bioorganic Chem.* 3, 133–140.

Short peptides capable of forming amphipathic helices are known to bind and penetrate lipid bilayers. See, Kaiser, E. T. and Kezdy, F. J. (1987) *Annu. Rev. Biophys. Biophysical Chem.* 15, 561–581; and Sansom, M. S. P. (1991) *Prog. Biophys. Molec. Biol.* 55, 139–235. Examples include model peptides like $(L-K-K-L-L-K-L-)_2$ (SEE SEQ ID NO: 1) which are disclosed in DeGrado, W. F. and Lear, J. D. (1985) *J. Am. Chem. Soc.* 107, 7684–7689, and the 26-residue bee venom peptide, melittin, disclosed in Watata, C. and Gwozdzinski, K. (1992) *Chem-Biol. Interactions* 82:135–149).

Possible mechanisms for the binding include alignment of peptide monomers parallel to the surface of the bilayer mediated by electrostatic interactions between polar amino acids and phospholipid headgroups, and insertion of peptide aggregates into the apolar bilayer core, stabilized, in part, by the hydrophobic effect. See, Sansom, M. S. P. (1991) *Prog. Biophys. Molec. Biol.* 55, 139–235.

VIP belongs to a family of homologous peptides, other members of which are peptide histine isoleucine (PHI), peptide histidine methionine (PHM), growth hormone releasing factor (GRF), pituitary adenylate cyclase activating peptide (PACAP), secretin and glucagon. The sequences of the family of homologous peptides follow (see SEQ ID NOS: 2–11, respectively). Identities with the VIP sequence are shown by underlining as are the conserved basic residues.

| | |
|---|---|
| VIP | HSDAVFTDNYTRLRKQMAVKKYLNSILN |
| rat GRF | HADAIFTSSYRRILGQLYARKLLHEIMNRQQGERNQEQRSRFN |
| human GRF | YADAIFTNSYRKVLGQLSARKLLQDIMSRQQGESNQERGARARL |
| PHM | HADGVFTSSYRRILGQLSAKKYLESLM |
| Secretin | HSDGTFTSELSRLRDSARLQRLLQGLV |
| Glucagon | HSQGTFTSDYSKYLDSRRAQDFVQWLMNT |
| PACAP | HSDGIFTDSYSRYRKQMAVKKYLAAVLGKRYKQRVKNK |
| Helospectin | HSDATFTAEYSKLLAKLALQKYLESILGSSTSPRPPSS |
| Helodermin | HSDAIFTQQYSKLLAKLALQKYLASILGSRTSPPP |
| Mellltin | GIGAVLKVLTTGLPALISWIKRKRQQ. |

Like VIP, these peptides could form amphipathic helices capable of binding lipids bilayers. In the present invention, VIP was used as the model peptide to show that the biological potency of this family of peptides is increased by expression in and on lipid bilayers.

The biological action of VIP and GRF are believed to be mediated by protein receptors expressed on the cell-surface and intracellular receptors. We have shown that the calmodulin is the likely intracellular receptor for VIP. See Paul et al., "Vasoactive Intestinal Peptide: Its Interactions with Calmodulin and Catalytic Antibodies", *Neurochem. Int.*, Vol. 23, No. 3, pp. 197–214 ; Stallwood et al. "Identity of a membrane-bound vaso active intestinal peptide binding peptide binding protein with calmodulin.", *J. Biol. Chem.*, Vol. 267, (1992), pp. 19617–19621; Stallwood et al. "Is calmodulin a neuropeptide receptor?" *FASEB J.*, Vol. 7, (1993), p. 1054 (abstr.) , the contents of these documents are expressly incorporated herein by reference. We speculated that intracellular delivery of VIP alone or VIP-calmodulin mixtures bypasses the requirement for cell-surface binding of the peptide and thus enhances the biological actions of the peptide. Provision of the peptides expressed in and on liposomes would achieve intracellular delivery, since the lipid bilayers of liposomes are known to fuse with the plasma membrane of cells and deliver their contents into the intracellular compartment.

A major factor limiting the therapeutic use of VIP has been its reduced bioavailability at target tissues because of proteolytic degradation and a multiplicity of conformations adopted by this peptide.

SUMMARY OF THE INVENTION

An objective of the invention is to provide a method of delivering to target tissues peptides belonging to the VIP- GRF family a vasoactive intestinal polypeptide (hereinafter "VIP") which overcomes the problems of conventional methods.

Another objective of the invention is to improve the efficacy and duration of VIP.

The invention relates to a method of delivering VIP to the surface and intracellular compartment of a target tissue of a mammal comprising the steps of forming a VIP liposome product where VIP is expressed on and in the liposome and administering an biologically effective amount of the VIP Liposome product to the target tissue.

Another embodiment of the invention relates to a VIP liposome product composed of cholesterol, phosphatidyl choline, and phosphatidyl glycerol.

A further embodiment of the invention relates to a method of making a VIP liposome product having increased biological potency and decreased side effects comprising the steps of forming the VIP liposome product under conditions where the resultant liposome product has VIP expressed on and in the liposome which comprises cholesterol, phosphatidyl choline, and phosphatidyl glycerol. "[e]xpressed on or in the liposome" is intended to mean the following. "On" connotes that VIP is exposed to the outside solvent and immobilized on the outside surface by insertion into the hydrophobic core of the lipid bilayer as explained in example 2 below.

"In" connotes soluble VIP in the luminal space of the liposomes and on the intraluminal face of the lipid bilayer of the liposomes. All forms of VIP in this liposome construct are likely to be in the helical conformation due to complexation with lipid molecules. Other objects, features, and characteristics of the invention will become apparent upon consideration of the following description and the appended claims.

DETAILED DESCRIPTION OF THE PREFERRED EMBODIMENTS

Figure 1:
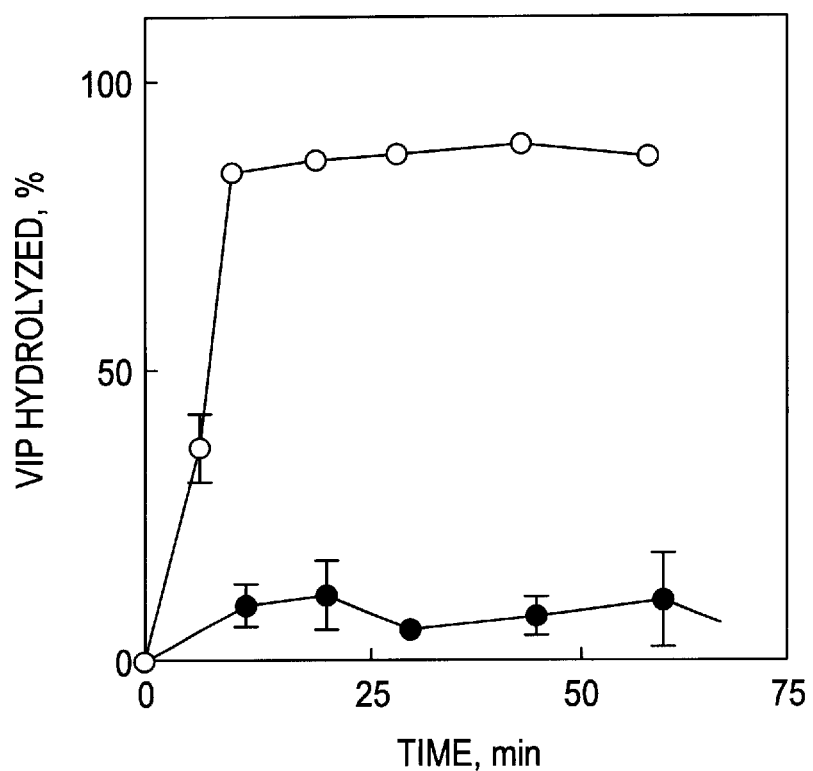
FIG. 1 illustrates the degradation by trypsin of the VIP expressed on and in liposomes (VIP liposome product) compared to a conventional VIP solution.

The invention relates to a method of delivering VIP to a target tissue of a mammal comprising the steps of forming a VIP liposome product where VIP is expressed on and in liposomes and administering a biologically effective amount of the VIP liposome product to the target tissue. A biologically effective amount refers to a concentration of VIP in the nanomolar to the micromolar range.

The VIP liposome product can be delivered intravenously, orally or transdermally where the transport system of the mammal delivers the VIP liposome product to the target tissue, or the VIP liposome product can be applied directly to the target tissue. Preferably, the VIP liposome product is delivered intravenously.

Preferably, the vasoactive intestinal polypeptide is expressed on and in liposomes comprising cholesterol, phosphatidyl choline, and phosphatidyl glycerol or other suitable lipid, (including synthetic and non-natural lipids).

Calmodulin, the intracellular receptor for VIP and GRF can be included along with the peptides in the liposomes. This permits delivery of VIP-calmodulin complexes into the cells of the target tissue and thus enhances peptide biological effects.

The vasoactive intestinal polypeptide can be, for example, HSDAVFTDNYTRLLRKQMAVKKYLNSILN-NH$_2$, (SEE SEQ ID NO: 12) fragments or analogs thereof, or peptides homologous to VIP, such as GRF, PHI, PHM, PACAP, secretin and glucagon.

Provision of the peptide expressed on and in lipid bilayers permits the peptides to reach the intracellular compartment, thus bypassing the requirement for binding to cell-surface receptors, and results in increased biological potency and efficacy of the peptides.

The vasoactive intestinal polypeptide can be bound in a helix conformation in the liposome. Preferably, the vasoactive intestinal polypeptide is bound in a receptor reactive conformation whereby a biological potency of the vasoactive intestinal polypeptide is enhanced.

The VIP liposome product can be administered at significantly reduced dosage levels compared to conventional VIP and yet achieve efficacy equal to the conventionally administered VIP. Generally, the biologically effective amount of VIP is about 50 to 75 percent less by weight than the biologically effective amount for the VIP in an encapsulated form. A biologically effective concentration of VIP is in the nanomolar to the micromolar range. Inclusion of calmodulin along with VIP at equimolar concentrations permits further reduction in the effective amount to 10% of that required using peptide administered by convention means.

VIP liposome product must be tested to determine the biologically effective amount required to achieve which comport with or exceed the results for conventionally administered VIP. For example, if the usual amount for VIP in conventional carriers is 20 mg, the VIP liposome product can achieve the same efficacy at about 10 mg to about 5 mg. Typically, the biologically effective amount for conventional VIP is 0.01 to 50 mg daily intravenously or 0.1 to 500 mg in enteric coated capsules, in humans.

The effects of VIP liposome product are also about 50 to about 100% longer lasting than conventional VIP.

The encapsulated VIP is significantly more resistant to hydrolysis than conventional VIP, which contributes to the increased longevity of encapsulated VIP.

The VIP is reversibly bound in the liposome.

The invention also relates to a VIP liposome product comprising cholesterol, phosphatidyl choline, and phosphatidyl glycerol.

The VIP can be bound in or on the liposome in a helix conformation. Preferably, the VIP is bound in a receptor reactive conformation whereby a biological potency of the VIP is enhanced.

A further embodiment relates to a method of making VIP having increased biological potency and decreased side effects comprising the steps of forming a VIP liposome product comprising cholesterol, phosphatidyl choline, and phosphatidyl glycerol.

Preferably, the VIP is bound in a receptor reactive conformation on or in the liposome.

Another embodiment relates to a method for controlling blood pressure in a mammal comprising the steps of administering an effective amount of a VIP liposome product comprising cholesterol, phosphatidyl choline, and phosphatidyl glycerol to the mammal.

The VIP liposome product can be used to treat, for example, abnormalities of gut motility, peptic ulceration, bronchial spasm including asthma, vascular conditions such as hypertension, impotence and ischaemia, mental disorders and baldness due to limiting blood flow.

The invention will be further explained using the following non-limiting examples.

EXAMPLE 1

The VIP release from liposomes according to the invention and the degradation of VIP bound on and in the liposomes was tested and compared to a conventional solution of VIP.

The hypotensive effect of VIP liposome product according to the invention was then compared to conventional VIP using Hamsters.

VIP liposome product was made using synthetic VIP (University of Florida, Gainsville) which was purified by successive reversed-phased HPLC on a preparative C-18 column in triethylamine phosphate/acetonitrile and trifluoroacetic acid (TFA)/acetonitrile solvent systems. The peptide content of the purified VIP was 82% and an amino acid analysis confirmed full length VIP.

Radioiodination of VIP and purification of $(tyr^{10}-^{125}I)VIP$ was done as described in Paul, S., Volle, D. J., Beach, C. M., Johnson, D. R., Powell, M. J. and Massey, R. J. (1989) *Science* 244, 1158–1162).

Liposomes were prepared by reverse evaporation from a mixture of egg yolk phosphatidylcholine, egg yolk phosphatidylglycerol and cholesterol (Sigma Chemical Co.) in a molar ratio of 1:4:5, using the method disclosed in Szoka, Jr., F. and Papahadjopoulos, *Proc. Natl. Acad. Sci.* USA 75, pp. 4194–4198 (1978). The phospholipids and cholesterol solution, 12 mM each, in 3 ml diethylether containing 3 mM synthetic VIP, a mixture of $(tyr^{10}-^{125}I)VIP$ (about 100,000 CPM) and 3 mM unlabeled VIP or 0.2 nM of radioactive peptide alone was mixed with 1 ml 50 mM HEPES, pH 7.3 and sonicated. The diethylether was evaporated in vacuo to form liposomes in the solution. The resulting suspension was diluted with 10 ml 50 mM HEPES, and then centrifuged at 12,500×g for 7 minutes. The supernant was discarded and the pellet washed three times with a buffer containing 0.15M NaCl. Large liposomes were removed using a 1 $\mu$m polycarbonate filter (Nucleopore). This method permits expression of VIP on the surface of liposomes and within liposomes.

The phospholipid content of the liposomes was measured by colorimetric determination of inorganic phosphate using the modified micro-assay method of Bartlett disclosed in Kates, M., "Techniques in Lipidology," pp. 354–356, 1972, Elsevier, N.Y.

The content of VIP in the liposomes was measured by two methods. In the first method, $(tyr^{10}-^{125}I)VIP$ (0.2 nM) mixed with 3 mM unlabeled VIP was encapsulated in liposomes and aliquots of the final liposome suspension were counted for $(tyr^{10}-^{125}I)VIP$ radioactivity (70% efficiency). In the second method, liposomes containing unlabeled VIP were solubilized with sodium dodecylsulfate (1% w/v), the extract was diluted to 0.01% SDS with 0.1% TFA in water and extracted on a Sep-Pak C18 cartridge (Waters), and the VIP content of the bound fraction was measured by radioimmunoassay as described in Paul, J. Chou and E. Kobota, *Life Sci.,* 41, pp. 2373–2380 (1987).

The degradation of VIP bound in the liposomes was tested and compared to a conventional solution of VIP as follows.

$(tyr^{10}-^{125}I)VIP$ in liposomes according to the invention, 17,700 cpm/0.67 $\mu$mole phospholipids, and an equivalent amount of $(tyr^{10}-^{125}I)VIP$ dissolved in 50 mM HEPES, pH 7.3, containing 0.5% bovine serum albumin (BSA, RIA grade; Sigma) were treated with 30 nM of trypsin from bovine pancreas (Sigma) at 23° C. Triton X-100 (Sigma) was added to 1% w/v to solubilize the liposomes. The detergent concentration was reduced to 0.25% with buffer.

Incubation 23° C. of the encapsulated $(tyr^{10}-^{125}I)VIP$ (solid circle) with trypsin over 60 minutes revealed little or no peptide hydrolysis, as shown in FIG. 1. In comparison, 80% of control $(tyr^{10}-^{125}I)VIP$ (hollow circle) in solution was digested within 10 minutes by the enzyme, as shown in FIG. 1. The values in FIG. 1 are means of 3 replicates±standard deviation.

The rate of trypsin-catalyzed hydrolysis of pro-phe-arg-methyleoumarinamide was essentially identical in the absence and presence of empty liposomes, which was measured as described S. Paul, et. al., *J. Biol. Chem.,* 267, pp. 13142–13145 (1992). The reduced hydrolysis of encapsulated VIP by trypsin, therefore, was not due to a non-specific inhibitory effect of the liposomes.

The peptide degradation by hydrolysis was measured by determining the trichloroacetic acid-soluble radioactivity of $(tyr^{10}-^{125}I)VIP$ as described in the Science 244:1158–1162 (1989) Supra.

The release of VIP from the liposomes was determined as follows.

The peptide release from liposomes containing $(tyr^{10}-^{125}I)VIP$, approximately 20,000 cpm, kept at 4° C. in 50 mM HEPES, pH 7.3, containing 0.02% $NaN_2$ was determined by centrifugation of aliquots of the suspension at 12,400×g for 15 minutes and measurement of radioactivity in the supernatants.

The leakage of $(tyr^{10}-^{125}I)VIP$ from the liposomes stored in buffer at 4° C. for 14 days was negligible, <2% of available radioactivity. Microscopic examination did not reveal breakdown of the liposomes over this time period.

The hypotensive effect of VIP liposome product according to the invention was compared to conventional VIP using male golden Syrian hamsters (120–130 g body weight) as follows.

The hamsters were first prepared by anesthetizing intravenously 6 mg of sodium pentobarbital per 100 g of body weight. A tracheostomy was then performed to facilitate spontaneous breathing. Supplemental anesthesia was administered intravenously as necessary at 2–4 mg/100 g body weight/hour. A femoral artery was cannulated for blood pressure monitoring. A femoral vein was cannulated for drug and florescent tracer administration.

The animals were kept on a heated pad throughout the duration of the experiment. Arterial blood pressure was recorded continuously using a pressure transducer and a strip-chart recorder (Model 7702B, Hewlett-Packard). The microcirculation of the hamster check pouch was visualized using intravital microscopy and clearance of fluorescein isothiocyanic-dextran (M.W.=70 RD; Sigma) from postcapillary venules and determined as described in W. G. Mayhan and I. Rubinstein, *J. Appl. Physiol.*, 75, pp. 27–32 (1993).

In each hamster, 1 ml aliquots of increasing concentrations of VIP dissolved in 0.15M sodium chloride or encapsulated in liposomes (1 nmol VIP/0.12 µmol phospholipids) were infused intravenously for 7 minutes.

The body weights of the control (125±2 g) hamsters and the experimental (124±1 g) hamsters were essentially identical.

Mean arterial blood pressure was recorded before, during, and for 60 minutes after administration of each concentration of the peptide.

In preliminary experiments, it was determined that infusion of 0.15M sodium chloride or empty liposomes was not associated with any significant change in mean arterial blood pressure (data not shown).

The number of leaky sites in check pouch microcirculation was determined every minute throughout the duration of the experiments as disclosed in W. G. Mayhan, Supra. The data is expressed as means±SEM. Students t-test for unpaired observations was used to compare responses to vasoactive intestinal peptide. A p value<0.05 was considered to be significant.

Encapsulated VIP prepared from a solution of tracer (tyr$^{10}$-$^{125}$I)VIP and 3 mM unlabeled VIP in the liposomes contained 8.9% of available peptide, corresponding to encapsulation of 0.008 mole VIP/mole phospholipid), measured on the basis of uptake of the radioactive peptide. This was measured by repeatedly washing the liposomes with saline to remove free peptide followed by determination of radioactivity in a gamma counter. Measurement of the amount of non-radioactive encapsulated VIP by radioimmunoassay yielded essentially identical values.

The effect on blood pressure was determined by measuring the magnitude of reduction in mean arterial blood pressure (MAP) as a function of time following infusion of VIP dissolved in saline or encapsulated in liposomes. The hamsters did not display detectable untoward effects during infusion of dissolved VIP or empty liposome preparations. In addition, no leaky site formation was observed in the check pouch microcirculation of the hamsters.

Figure 2:
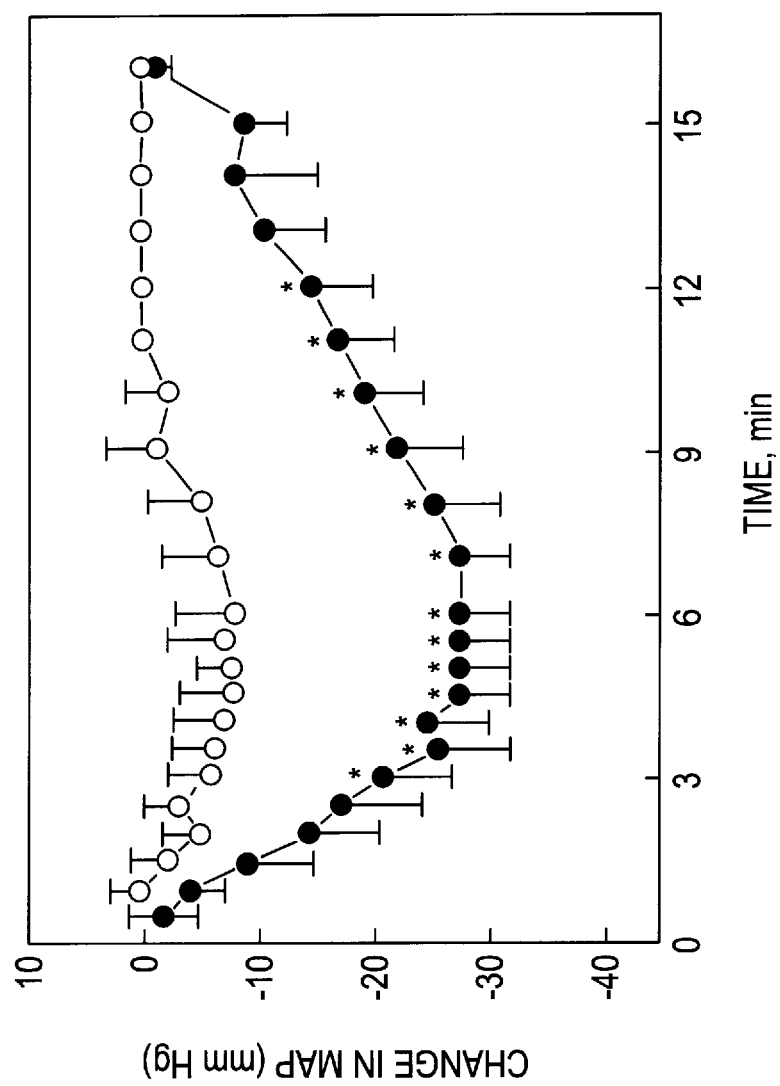
FIG. 2 illustrates the decrease in mean arterial blood pressure of hamsters treated with VIP liposome product and a conventional VIP solution.

FIG. 2. shows the decrease in MAP as a function of time during and following administration of VIP encapsulated in liposomes, 0.008 peptide/mole phospholipid, or dissolved in saline. The dosage level was 1.0 nmole for the encapsulated VIP and the VIP in 0.15M Nacl (saline) solution. The peptide infusion time was 7 minutes (solid bar). MAP values for animals treated with VIP in saline (hollow circles) or in liposomes (solid circles) were 93.0 and 93.4 mm Hg. The data is the means from 5 hamsters (±SEM) in each group. In FIG. 2, (*) represents P<0.05 versus VIP in saline at corresponding time points, with one-tailed t-test for unpaired observations.

As shown in FIG. 2, a significant decrease in MAP was observed at 5 minutes (p<0.05, one-tailed t-test) and marginally significant decreases were observed at other time points between 3 and 7 minutes (p<0.1). In comparison, infusion of VIP liposome product produced a significant decrease in MAP within 1.5 minutes. The magnitude of the maximum reduction in MAP was approximately 3.5 fold greater, and the duration of the hypotensive effect was more prolonged than with VIP dissolved in saline. At a dose of 1 nmole per hamster, VIP dissolved in saline only induced a weak and transient decrease in MAP, as shown in FIG. 2.

FIG. 2 illustrates that the effect of the VIP was fully reversible, indicated by return of the arterial blood pressure values to the pre-infusion baseline (VIP dissolved in saline, 9 minutes; VIP liposome product, 16 minutes).

Figure 3:
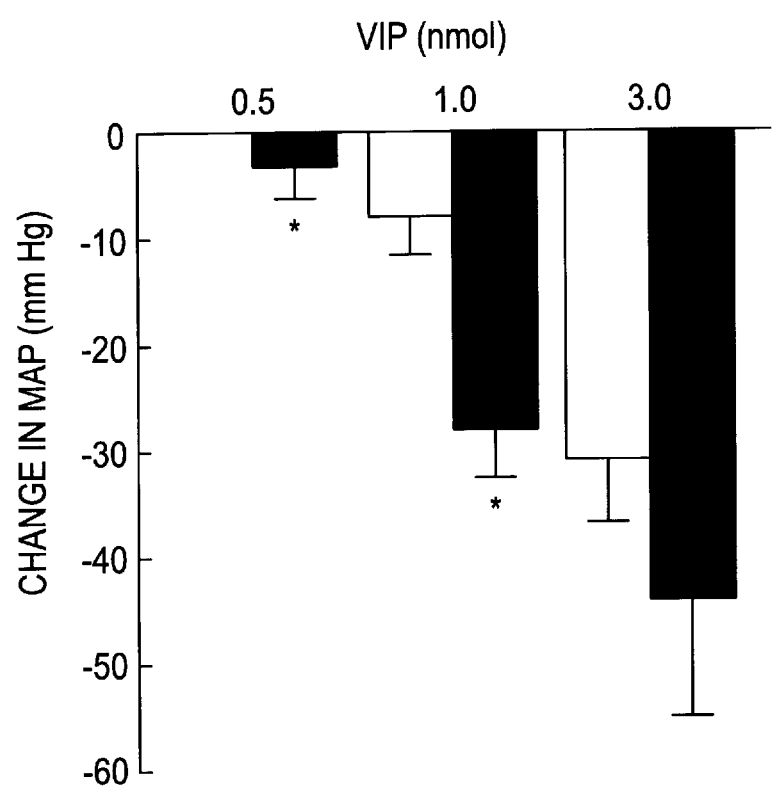
FIG. 3 illustrates the change in mean arterial blood pressure of hamsters compared to dosage amounts of VIP liposome product and a conventional VIP solution.

FIG. 3 illustrates the effect of VIP liposome product (0.008 mole peptide/mole phospholipid; solid bars) compared to VIP dissolved in 0.15M NaCl (hollow bars) on the mean arterial pressure (MAP) in anesthetized hamsters. The values are means±SEM (n=5). *p<0.05 versus VIP in saline.

The above data illustrates that the hypotensive effect of VIP in saline or encapsulated in liposomes is concentration dependent. The data further illustrates that the decrease in MAP following infusion of 0.5 nmole or 1 nmole VIP in liposomes was significantly greater than equivalent amounts of control VIP in saline (p<0.05).

At 3 nmole VIP, the values for control and peptide liposome product were not significantly different, because the dose produced a saturating peptide concentration.

This example illustrates that the hypotensive effect of VIP is significantly enhanced by presence of the peptide in and on liposomes. This is evident both by a prolongation of the hypotensive effect and an increase in the magnitude of the effect observed using VIP liposome product compared to control VIP solutions. Administration of empty liposomes had no significant effects on mean arterial blood pressure. There was no evidence of microvascular injury following administration of empty liposomes or VIP liposome product. In addition, the hypotensive effects of VIP alone or VIP liposome product were fully reversible. Collectively, the data demonstrates that non-specific tissue injury was not a contributory factor in the enhanced hypotensive effect of VIP contained in or on liposomes.

The reduced trypsinolysis of VIP liposome product demonstrates that diminished degradation of VIP could underline the increased duration of its hypotensive effect in Hamsters. In view of the amphipathic character of VIP, the applicants believe that the lipids bind VIP and enhance its biological potency by stabilizing a receptor-reactive conformation. This is supported by observations that VIP penetrates protein-free bilayers as described in Y. Noda, et. al., *FASE B. Journal* 7, 1053 (1993), and anionic lipids like phosphatidyl glycerol induce helix formation in the peptide detected by circular dichroism studies disclosed in R. M. Robinson, et. al., *Bipolymers*, 21, pp. 1217–1228 (1982). A correlation between the helix forming tendencies of VIP analogues and their biological potencies is described in G. F. Musso, et. al., *Biochemistry*, 27, pp. 8174–8181 (1988).

EXAMPLE 2

Demonstration of Lipid Bilayer Binding and Penetration by VIP

The VIP release from liposomes according to the invention and the degradation of VIP bound in the liposomes was tested and compared to a conventional solution of VIP.

Unilaminar phospholipid liposomes were formed using phosphatidylcholine (PC) and phosphatidylglycerol (PG) purified from egg yolk (Sigma). The fatty acid composition of the phospholipids determined by Sigma was: (PC, C16:0), (35%; C18:0, 12%; C18:1, 31%; C18:2, 14%); (PG, C16:0, 30%, C18:0, 13%; C18:1, 30%; C18:2, 16%). The unilamellar liposomes were prepared by reverse-phase evaporation as disclosed in Szoka, Jr., F. and Papahadjopoulos (1978) *Proc. Natl. Acad. Sci.* USA 75, 4194–4198), from a mixture of PG/PC/CH(cholesterol) (molar ratio 1:4:5) or PC/CH (1:1) dissolved in chloroform.

The lipid solution was taken to dryness using a rotary evaporation and then dissolved in 3 ml diethylether. The phospholipid and cholesterol (CH) concentrations were 12 mM each and 1 ml 50 mM HEPES, pH 7.3 was then added to the suspension and the suspension was sonicated for 2 minutes in ice using a bath sonicator (Branson).

The suspension was evaporated under reduced pressure for 20 minutes at 20°–25° C., diluted with 10 ml of 50 mM HEPES, pH 7.3. The suspension was then centrifuged at 12,500×g for 7 minutes, the supernatant was discarded, and the pellet containing liposomes was resuspended in a HEPES buffer, pH 7.3.

The suspended liposomes were stored at 4° C. in buffer containing 0.02% sodium azide and used within ten days of preparation. Microscopic observation did not indicate aggregation or disintegration of the liposomes over this period of time.

The phospholipid content of the liposomes was measured by colorimetric determination of inorganic phosphate ($P_i$) using the modified microassay method of Bartlett described in Kates, M. In: Techniques in Lipidology, pp. 354–356, 1972, Elsevier, N.Y. The liposome concentrations are expressed in $P_i$ units.

Electron microscopy (Philips 410 LS) on a FORMVAR polyvinyl formaldehyde plastic-coated grid after negative staining of the liposomes with an equal volume of 1% ammonium molybdate w/v in 50 mM HEPES, pH 7.3, revealed that greater than 90% of the liposomes were between 200 nm and 1000 nm in diameter. See, Johnson, S. M., Bangham, A. D., Hill, M. W. and Korn, E. D. (1971) *Biochem. Biophys. Acta* 233, 820–826.

Synthetic VIP (HSDAVFTDNYTRLLRKQMAVKKYLNSILN-NH2; SEQ ID NO: 12; peptide content 81%, Bachem) was labeled with $^{129}$I using chloramine-T. The (tyr$^{10}$-$^{125}$I) VIP was separated by reversed-phase high performance liquid chromatography (RP-HPLC) and identified by N-terminal radiosequencing as described in Example 1. The specific activity of the peptide was 2000 Ci/mmole.

Unlabeled VIP synthesized at the University of Florida, Gainesville and purified by preparative RP-HPLC on a C-18 column was used in some of the examples. The peptide content of this preparation was 83% and the purity was confirmed by amino acid analysis and automated N-terminal sequencing at the University of Nebraska Protein Structure Core Facility.

Peptide was permitted to bind liposome surface in aqueous solution. In organic solvents as in Example I, the peptide will be expressed in as well as on the lipid membranes of liposomes.

The liposomes were the pelleted (12,000×g, 10 min; Beckman centrifuge MICROFUGE®). The supernatant was aspirated and the liposome-associated radioactivity was measured at 70% efficiency (Beckman model 5500 gamma counter). There was minimal loss of the liposomes in the supernatant, because more than 90% of the inorganic phosphate present in the reaction mixture was recovered in the pellet.

The liposomes were solubilized with 20% acetonitrile (final concentration) for 10 min at 23° C. and CF fluorescence was determined ($\lambda_{cru}$ 520 nm, $\lambda_{ex}$ 490 nm; Perkin-Elmer LS50 fluorimeter). In a control experiment, the fluorescence intensities of liposomes (2.3 mM P) mixed with known concentrations of CF in the absence and presence of 20% acetonitrile were found to be essentially identical.

The resistance to hydrolysis of liposome-bound and free (tyr$^{10}$-$^{125}$I)VIP was tested by adding Trypsin (Sigma) in 50 mM HEPES, pH 7.3 thereto. The liposomes were centrifuged to separate released radioactivity, solubilized in 20% acetonitrile, BSA was added to 0.1% (w/v) as carrier and the TCA-insoluble radioactivity (undegraded VIP) was determined according to Paul, S., Volle, D. J., Beach, C. M., Johnson, D. R., Powell, M. J. and Massey, R. J. (1989) *Science* 244, 1158–1162.

The levels of VIP hydrolysis determine by this method correlated with those observed by separation of the reaction mixtures by RP-HPLC (r>0.9) as reported in Paul, S., Mei, S., Mody, B., Eklund, S. H., Beach, C. M., Massey, R. J. and Hamel, F. (1991) *J. Biol. Chem.* 266, 16128–16134. Hydrolysis of pro-phe-arg-MCA (Peptides International) was determined as the fluorescence of the coumarin leaving-group ($\lambda$ em 460 mn, $\lambda$ ex 370 nm).

The binding data was corrected for peptide adsorption by the reaction tubes determined in parallel incubations.

Dissociation and saturability data were analyzed by means of Kinetic and Enzfitter (Elsevier Biosoft).

Binding of carboxyfluorescein (CF; 100 nM; Eastman Kodak) was measured using experimental conditions identical to those used for VIP.

The ESR was taken as follows. Lipid liposomes were prepared as described above, except that 5-doxyl-stearic acid (5-DS) or 16-doxyl-stearic acid (16-DS) (Sigma) was included in the phospholipid solution in ether to give a spin label concentration of 0.2 nM (spin label/phospholipid molar ratio, 1.60). The labeled liposomes were washed, and incubated with VIP in 0.2 ml 50 mM HEPES, pH 7.3, 0.5% BSA (w/v) at 23° C. for 60 min. After incubation, the labeled liposomes were centrifuged at 12,000 rpm for 15 min and the resulting pellet was resuspended in 100 µl of 50 mM HEPES, pH 7.3.

The Electron Spin Resonance (ESR) spectra were recorded as described in Hiramatsu, M., Edamatsu, R., Velasco, R. D., Ooba, S., Kanakura, K. and Mori, A. (1993) *Neurochem. Res.* 18, 313–316, at 27°±0.5° C. using a JES-FE1XG ESR spectrometer (JOEL, Tokyo) with instrumental parameters as follows: 9.0060 GHz microwave frequency, 0.2 mT modulation width at 100 kHz modulation frequency, response time 0.3 or 1.0 sec, sweep time 10 mT/2 min. microwave power 8 mW. The polarity-corrected order parameter S was calculated from the hyperfine splitting pattern according to Hubbel, W. L. and McConnel, N. M. (1971) *J. Am. Chem. Soc.* 93, 314–326, from the 5-DS spectra and the motion parameter T_corresponding to the rotational correlation time, from the 16-DS spectra according to Eletr, S. and Inesi, G. (1972) *Biochim. Biophys. Acta* 290, 178–185.

The binding of the VIP to the liposome was determined as follows. Unilamellar lipid liposomes were prepared by reverse evaporation and assayed for binding of radiolabeled VIP, as described above. BSA was included in the assay diluent to saturate nonspecific polypeptide binding sites in the lipid liposomes and the polypropylene surface of the reaction tubes.

Increasing concentrations of preformed lipid liposomes (2.5–45.6 mM $P_i$) displayed increasing binding of (tyr$^{10}$-$^{125}$I)VIP, up to 56.6% of available peptide (0.42 nM). The results are shown in Table 1.

Under conditions identical to those used for VIP, the liposomes took up very small amounts of carboxyfluorescein, which is a small polar molecule (376 daltons) often used to study the integrity of lipid liposomes.

In contrast, liposomes formed in the presence of VIP and CF contained somewhat greater concentrations of CF than VIP. The latter values represent encapsulation of VIP and CF within liposomes. Taken together, the data illustrates that the observed association of VIP with the liposome does not represent entrapment due to liposome breakage and resealing.

TABLE 1

| Probe | Binding, nM | Encapsulation, nM |
|---|---|---|
| VIP | 20.5 ± 1.0 | 37.5 ± 5.0 |
| CF | 0.01 ± 0.001 | 82.5 ± 7.5 |

Values are means±s.d. Probe-binding was with pre-formed liposomes (2.3 mM $P_i$) and 100 nM CF or 0.2 nM ($tyr^{10}$-$^{125}I$)VIP mixed with 100 nM unlabeled peptide. Encapsulation was by making liposomes from lipid solutions (2.6 mM $P_i$) containing 2.5 μM CF or 1.7 nM ($Tyr^{10}$-$^{125}I$)VIP mixed with 2.5 μM unlabeled VIP. Free probes were removed by three washes with 50 mM HEPES, pH 7.3, containing 0.5% BSA. CF values were determined by fluorimetry after solubilization of liposomes, and VIP values, by measurement of liposome-associated radioactivity.

Figure 4:
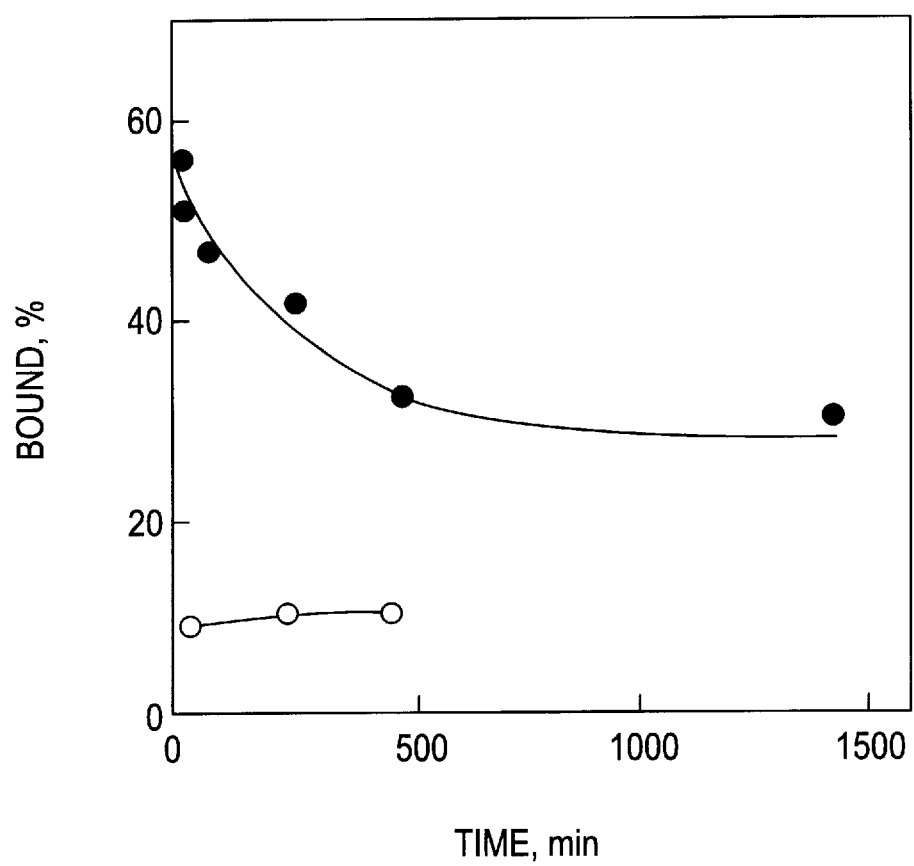
FIG. 4 illustrates the percent release of $(tyr^{10}\text{-}^{125}I)VIP$ bound on lipsomes of bound VIP over time by dilution into solutions without VIP (closed circles) or excess unlabeled VIP (open circles).

Incubation of ($Tyr^{10}$-$^{125}I$)VIP-liposome complexes in the presence of excess unlabeled VIP (2 mM) resulted in release of approximately 90% of the initial liposome-associated peptide and steady-state conditions were reached at the earliest time-point examined (30 min), showing that the peptide was not irreversibly sequestered in the lipid bilayers. In the absence of exogenous unlabeled peptide, slow release of approximately 50% of the liposome-associated peptide over 24 h was observed, as shown in FIG. 4.

The reversibility of binding of VIP by lipid liposomes was measured as followed. Liposomes (3.3 mM 0) were labeled with ($Tyr^{10}$-$^{125}$)VIP (0.11 nM), washed to remove free peptide and incubated in 0.2 ml buffer in the absence (hollow circle) or presence of (black circle) of 2 mM unlabeled VIP for varying time-periods (20° C.). The remaining liposome-associated radioactivity was determined and expressed as % of initial bound peptide (35,410 CPM).

Figure 5:
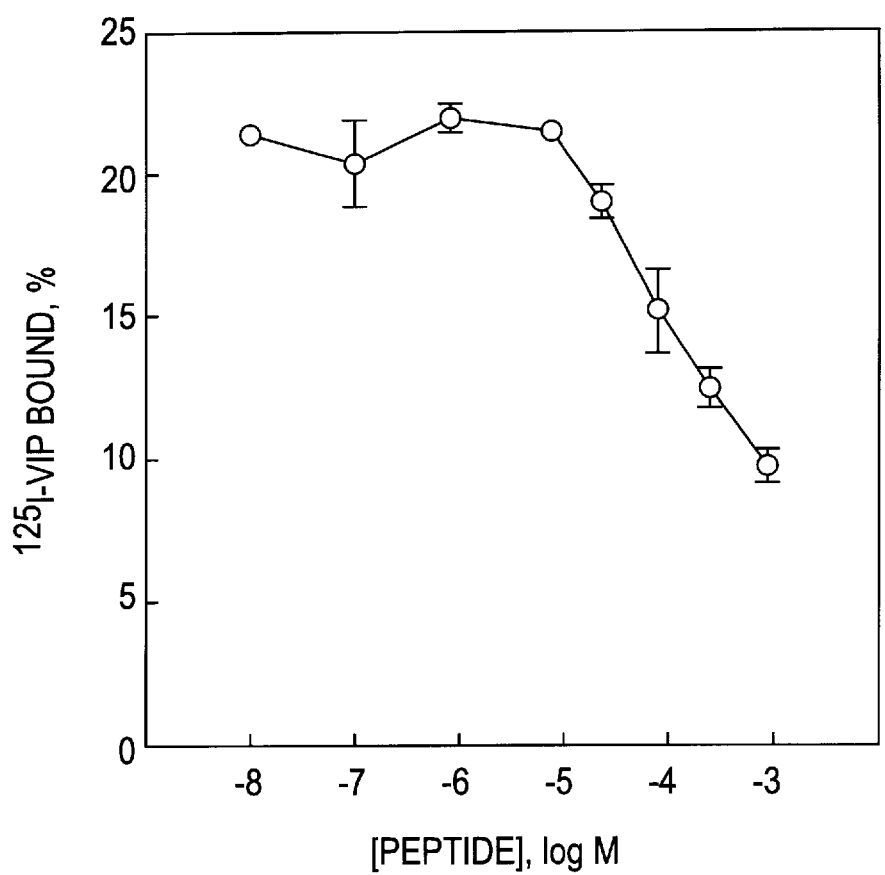
FIG. 5 illustrates competitive inhibition of binding of $(tyr^{10}\text{-}^{125}I)VIP$ on liposomes by unlabeled VIP.

The partitioning of ($Tyr^{10}$-$^{125}I$)VIP into the liposomes was competitively inhibited by increasing concentrations of unlabeled VIP (IC50 560 μM;), as shown in FIG. 5. A plot of bound versus available peptide can be fitted to the equation for a rectangular hyperbola typical of a saturation isotherm [$y=(B_{max}\cdot x)/(1/K+y)$, where x and y are available and bound peptide, respectively].

FIG. 5 illustrates the results of the competitive inhibition of binding of ($Tyr^{10-125}$)VIP (0.26 nM) by the liposomes (2.4 mM $P_i$) by unlabeled VIP (10 nM-1 mM). Data are means±s.d expressed as % of available radiolabeled peptide.

Figure 6:
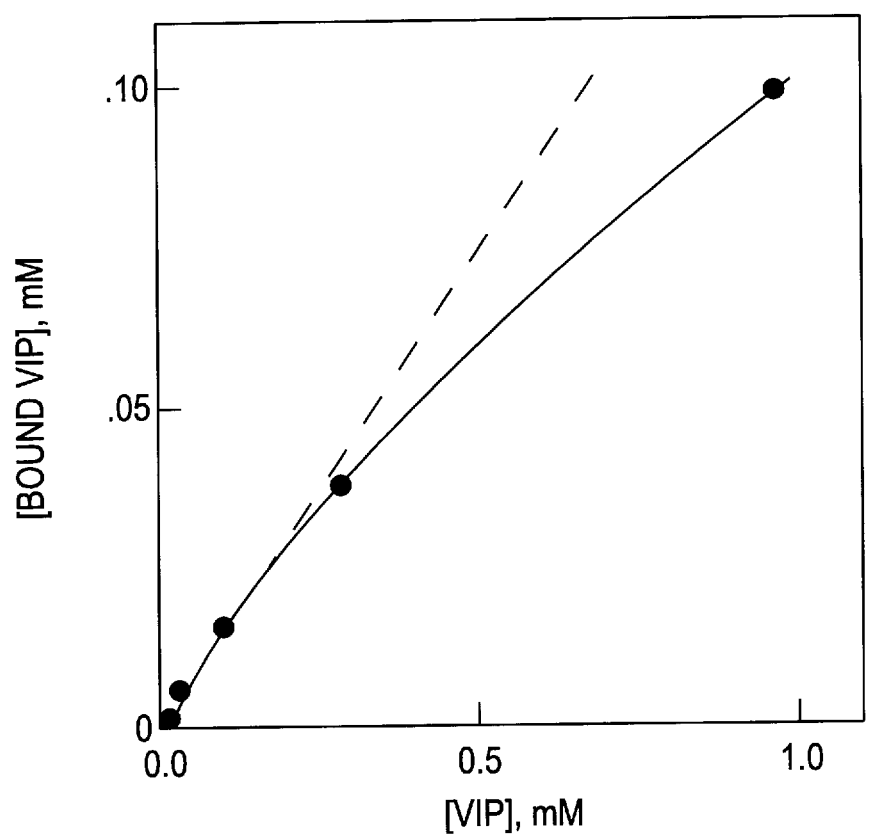
FIG. 6 illustrates competitive inhibition of binding of $(tyr^{10}\text{-}^{125}I)VIP$ on liposomes by having unlabeled VIP.

FIG. 6 illustrates a saturation isotherm constructed from the data in FIG. 5 (solid line). The dotted line shows the levels of binding expected in a non-saturable reaction.

In a control experiment performed to eliminate the possibility of artifacts due to use of radiolabeled peptide, lipid liposomes (2 mM $P_i$) were permitted to bind unlabeled VIP (0.2 mM), the liposomes were solubilized with 1% SDS and extracted on a C-18 cartridge and analyzed by RP-HPLC on a C-18 column according to Paul, S., Volle, D. J., Beach, C. M., Johnson, D. R., Powell, M. J. and Massey, R. J. (1989) *Science* 244, 1158–1162. A peptide peak displaying the characteristic retention time of authentic VIP was observed. The amount of peptide recovered in this peak, estimated by its absorbance at 214 nm, was 76% of the value predicted from radiolabeled VIP-binding experiments.

The binding of VIP (100 nM) by electrically neutral and negative liposomes prepared from PC/CH and PG/PC/CH, respectively, was compared. In each case, the levels of peptide binding increased within increasing concentration of the liposomes. The values of % VIP bound±s.d./μmol $P_i$ were, PG/PC/CH liposomes, 26.2+3.4; PC/CH liposomes, 12.6±1.5. Provided that minor differences in fatty acid composition of the phospholipids are not an interfering factor, this data is consistent with a stabilizing role for electrostatic interactions between acidic lipid head groups and VIP, which is a basic peptide rich in lys and arg residues. The inclusion of cholesterol, an agent that can be expected to decrease bilayer fluidity at the temperatures used in this study, as reported in Demel, R. A. and DeKruyff, B. (1976) *Biochim. Biophys. Acta* 457, 109–132), did not influence the binding of VIP by the liposomes (26.2% and 24.9% VIP bound/μmole $P_i$ PC/PG/CH and by PC/PG liposomes respectively.)

Figure 7:
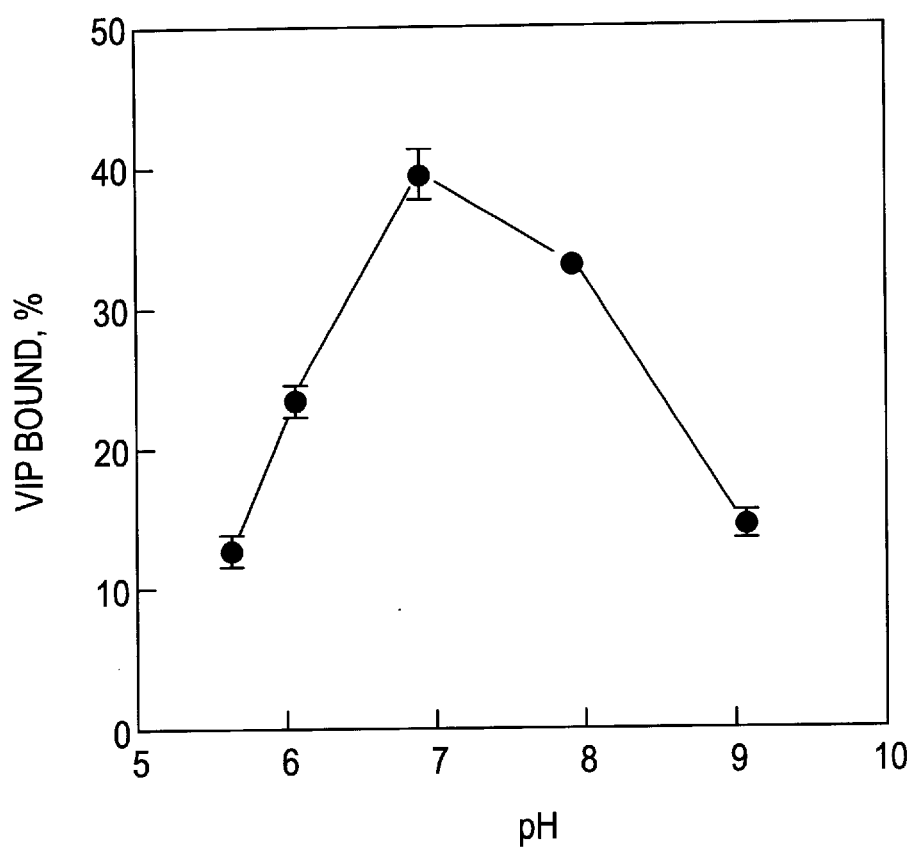
FIG. 7 illustrates pH dependency of binding of $(tyr^{10}\text{-}^{125}I)VIP$ on liposomes.

The solvent effects on the encapsulated VIP were measured as follows. In particular, pH-dependent binding of ($Tyr^{10}$-$^{125}$)VIP (0.14 nM) by lipid liposomes (2.1 mM $P_i$) was assayed at several pH values in a constant ionic strength buffer (25 mM ethanolamine, 25 mM Tris, 50MM morpholinethane sulfonic acid) as disclosed in Ellis, K. J. and Morrison, J. F. (1982) *Meth. Enzymol.* 87, 406–427). The results are shown in FIG. 7, which illustrates that the binding was low at the extreme pH values and optimal binding was observed at near-neutral pH (pH 6–8). The data are means± s.d from a representative experiment.

Treatment of ($Tyr^{10}$-$^{125}I$)VIP-liposome complexes with 25 mM EDTA, 1 mM HCl, or 1M NaCl caused little or no release of the bound peptide, as shown in Table 2. At alkaline pH (1mM NaOH), a small but significant proportion (16) of the bound radioactivity was reproducibly released. Dissolution of the liposomes with SDS produced near-complete peptide release into the supernatant, reflecting, presumably, uptake of the peptide into mixed detergent-lipid micelles.

TABLE 2

| Treatment | % VIP released |
|---|---|
| 25 mM EDTA | 8.1 ± 10.0 |
| 1 mM HCl | 3.0 ± 3.5 |
| 1 M NaCl | 2.7 ± 3.0 |
| 1 mM NaOH | 15.9 ± 4.0 |
| 1% SDS | 81.1 ± 9.6 |

Lipid liposomes (4 mM $P_i$) were permitted to bind ($Tyr^{10}$-$^{125}I$)VIP (1 nM), washed extensively to remove unbound radioactivity and then treated twice with 1 ml of the indicated solutions for 10 min (23° C.). Released radioactivity was determined in the pooled supernatant obtained by centrifugation. Values are % of initial liposome-bound radioactivity (76,300 CPM), corrected for peptide release in control incubations performed in 50 mM HEPES, pH 7.3 (4.2±3.4%).

Figure 8:
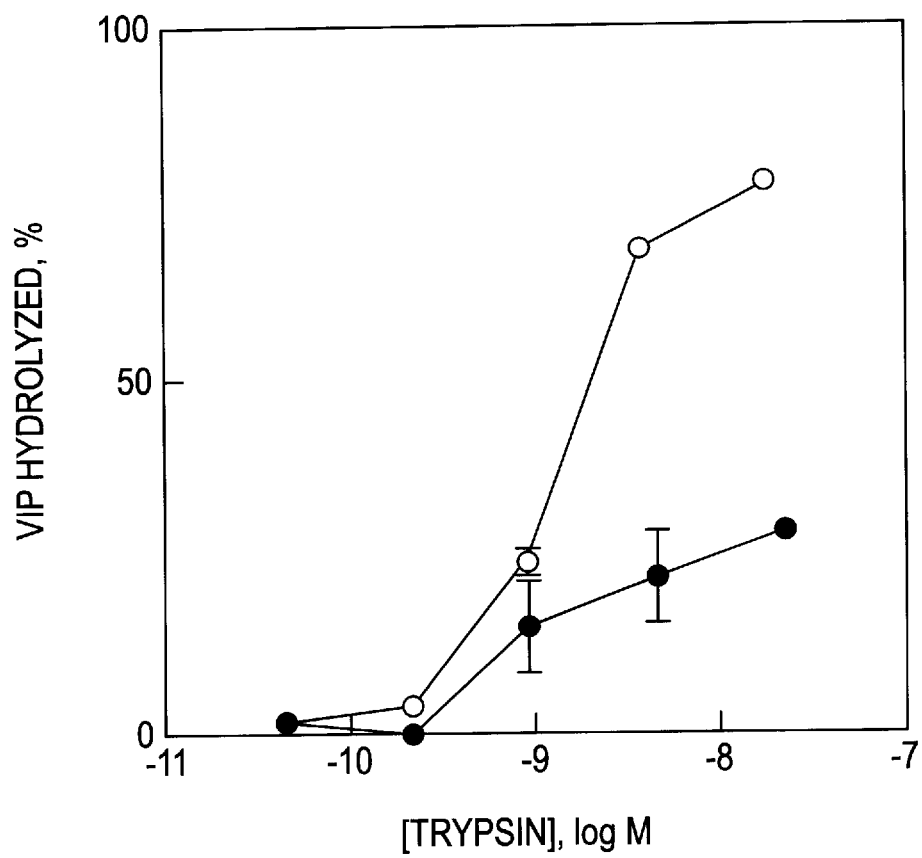
FIG. 8 illustrates the degradation by proteolytic hydrolysis of the VIP bound on liposomes compared to a conventional VIP solution.

The degradation of VIP liposome product was measured. With increasing trypsin concentration, increasing hydrolysis of free ($Tyr^{10-125}I$)VIP after 45 min of incubation (up to 80% of available peptide) was evident, as shown in FIG. 8. In the case of liposome-bound ($Tyr^{10}$-$^{125}I$)VIP, most of the radioactivity remained associated with the liposomes treated with 1 nM, 5 nM and 26 nM trypsin (82, 83 and 73% of initial radioactivity, respectively). Compared to the free peptide, a smaller proportion of the liposome-associated radioactivity recovered after the trypsin-treatment was TCA-soluble, suggesting a reduced susceptibility to proteolysis. To test for nonspecific inhibition of enzyme activity, a methylcoumarinamide (MCA) conjugate of a basic peptide (pro-phe-arg-MCA) (15 $\mu$M) (SEE SEQ ID NO: 13) was incubated with trypsin (10 nM) in the absence and presence of the liposomes (1 mM $p_i$) for 30 minutes, followed by removal of the liposomes by centrifugation. The observed increases in fluorescence intensity in the presence and absence of the liposomes were similar (868 FU and 885 FU, respectively).

FIG. 8 shows decreased proteolytic hydrolysis of liposome-bound VIP (hollow circle) compared to free VIP (black circle). Liposomes (4.2 mM $P_i$) were labeled with (Tyr$^{10}$-$^{125}$)VIP (0.37 nM), washed with buffer to remove free peptide and treated with varying concentrations of trypsin for 45 min n 50 mM HEPES, pH 7.3. Released radioactivity was removed by centrifugation and aspiration of the supernatant. Liposomes were solubilized with acetonitrile (30%). TCA was added to 10% and BAS to 0.1%, and acid-soluble radioactivity was measured to determine the degree of hydrolysis. Data are means±s.d expressed as % of initial liposome-associated peptide (28,290 CPM) corrected for TCA-soluble radioactivity observed in the absence of trypsin (10%).

The VIP effects on bilayer fluidity were determined. ESR spectra of 5-DS and 16-DS labeled lipid liposomes were first obtained. These spin labels are commonly used to measure the fluidity close to the surface (5-DS) and core (16-DS) of lipid bilayers (e.g., 117.22). With increasing VIP/lipid molar ratios, progressively decreasing values of the motion parameter $\tau_o$ were evident using 16-DS labeled liposomes, as shown in Table 3.

In contrast, the order parameter S computed using the 5-DS probe tended to increase by exposure to VIP, with the effect reaching statistical significance at a concentration of 500 $\mu$M VIP. This data suggests a pronounced VIP-induced increase of fluidity in the hydrophobic core of the bilayer and a relatively small but significant decrease in fluidity close to the bilayer surface.

TABLE 3

| VIP, $\mu$M | S (5-DS) | $\tau_o$, X10$^{-10}$ sec (16-DS) |
| --- | --- | --- |
| 0 | 0.751 ± 0.014 | 136.06 ± 22.01 |
| 200 | 0.755 ± 0.012 | 121.71 ± 32.41 |
| 300 | 0.771 ± 0.017 | 91.85 ± 9.31* |
| 500 | 0.801 ± 0.031* | 88.43 ± 2.65* |

Concentrations of PC/PG/CH liposomes were 2.8 mM $p_i$ (5-DS) and 3.7 mM $P_i$ (16-DS). Values of S and $\tau_o$ for 5-DS and 16-DS labeled liposomes, respectively, are means±SD from 3 (5-DS) or 4 (16-DS) experiments. *p<0.05 versus control values (liposomes in the absence of peptide) calculated by ANOVA.

The general conclusion from this Examples is that VIP can bind and penetrate the hydrophobic core of model lipid bilayers. The binding was saturable and reversible at neutral pH. The nominal values of the partition constant derived from the binding isotherm (1.4×10$^{-3}$M$^{-1}$) was in the same range as that reported for another amphophilic peptide, melittin, in Beschiaschvili, G. and Seelig, *J. Biochemistry* 29, 52–58. The apparent binding capacity at saturating VIP concentrations was 1 mol VIP/12.5 mol phospholipid.

Electrostatic interactions probably play a role in the observed VIP binding by PG containing negatively-charged liposomes, because VIP is a basic peptide. However, several considerations indicate that electrostating binding alone cannot explain the observed interaction because: (a) Neutral liposomes also displayed VIP binding activity, in contrast to observations that several other basic peptides are bound only by negatively charged liposomes as reported in Mosior, M., and McLaughlin, S. (1992) *Biochemistry* 31, 1767–1773; (b) VIP bound by PG/PC/CH liposomes was released minimally or not at all by acid, alkali and high ionic strength solvent; (c) the optimal pH for VIP binding by negatively charged liposomes was in the neutral range, unlike alkaline pH optima observed for the binding of basic proteins like lysozyme by similar liposomes as disclosed in Bergers, J. J., Vingerhoeds, M. H., van Bloois, L., Herron, J. N., Janssen, L. H. M., Fischer, M. J. E. and Crommelin, D. J. A. (1993) *Biochemistry* 32, 4641–4649); and, (d) treatment with VIP produced significant changes in the mobility of introxide spin-labeled stearic acid probes incorporated in the lipid liposomes. These considerations are consistent with the hypothesis of electrostatic binding of VIP to phospholipid head groups combined with penetration of a hydrophobic region(s) of the peptide into the bilayer.

Estimates of the fluidity at different depths in the bilayer can be obtained by measuring the motion of spin labels placed at varying distance from the carboxyl group of fatty acid probes (e.g., 5-DS and 16-DS used in the present study). Binding of polypeptides by membranes can lead to qualitatively similar or opposing effects on fluidity at different depths in the bilayer. See Boggs, J. M. (1983) in *Membrane Fluidity in Biology* (Aloia, R. C. ed.) Vol II, pp. 89–130, Academic Press, N.Y. for review. In this Example, the association of VIP with the liposomes was accompanied by a small but significant increase in the order parameter S for 5-DS and a striking decrease in the motion parameter $\tau_o$ for 16-DS, suggesting decreased fluidity close to the surface of the bilayer and increased fluidity in its core.

Myelin basic protein, as disclosed in Boggs, J. M., Wood, D. D. and Moscarello, M. A. (1981) *Biochemistry* 20, 1065–1073, has been previously described to produce similar effects on the fluidity characteristics in the bilayer core and surface. The decrease in 5-DS mobility following exposure to VIP may derive from electrostatic binding at phospholipid head groups. In analogy with the mechanism proposed for myelin basic protein, penetration of a hydrophobic region of VIP into the bilayer may produced a larger volume increase in the core of the bilayer compared to its surface, accounting for the increased mobility (decreased $\tau_o$) to the 16-DS probe.

The lipid binding properties of VIP are not entirely unexpected in the context of its known structural characteristics. Modeled as a $\pi$-helix (4.4 residues/turn) or a twisted $\alpha$-helix (Musso, G. F., Patthi, S., Ryskamp, T. C., Provow, S., Kaiser, E. T. and Velicelebi, G. (1988) *Biochemistry* 27, 8174–8181), the cationic and apolar resides of VIP segregate onto the opposite faces of the helix. $\alpha$-helical amphiphilic peptides are well documented to bind lipid bilayers. For example, depending upon the experimental conditions, melittin and alamethicin may bind along the surface of lipid bilayers or form bilayer-spanning aggregates, as reported in Sansom, M. S. P. (1991) *Prog. Biophys. Molec. Biol.* 55, 139–235. Similarly, peptides in which $\alpha$-helix distortions permit segregation of apolar and polar residues are known to bind lipid bilayers, as reported in Karle, I. L., Flippen-Andersen, J., Uma, K. and Balaram, P. (1988) *Proc. Natl. Acad. Sci.* U.S.A. 85, 299–303. In the case of VIP, the central segment spanning residues 12–21 contains cationic residues interspersed with apolar ones, has a high propensity for helix formation, as reported in Robinson, R. M., Dlakeney, Jr., E. W. and Mattice, W. L. (1982) *Biopolymers* 21, 1217–1228; Hamed, M. M., Robinson, R. M. and Mattice, W. L. (1983) *Biopolymers* 22, 1003–1021; and Bodanszky, M. Bodanszyk, A., Klausner, Y. S. and Said, S. I. (1974) *Bioorganic Chem.* 3, 133–140), and could be important in formation of peptide aggregates with membrane binding activity. All of the trypsin-sensitive bonds in VIP are located in this region ($R^{12}$-$L^{13}$, $R^{14}$-$K^{15}$, $K^{15}$-$Q^{16}$ $K^{20}$-$K^{21}$, $K^2$-$Y_{22}$). The observation of diminished trypsinolysis of liposome-associated VIP is consistent with burial of this segment into the lipid bilayer.

The biological actions of VIP are remarkably diverse and this neuropeptide activates apparently unrelated signal transducing systems reviewed in Said, S. I. (1984) *Peptides* 5, (Suppl. 1) 149–150; Paul, S. and Ebadi, M. (1993) *Neurochem. Int.* 23, 197–214. VIP is a known modulator of synaptic transmission, smooth muscle tone, transmembrane water and ion flux, neuroendocrine secretion and T- and B-lymphocyte immunological activities. There are several ways in which VIP-lipid bilayer interactions may be important.

In the absence of definitive evidence concerning the mechanism or removal and inactivation of VIP, it was commonly assumed that proteolytic degradation is responsible for termination of the biological effects of the peptide. In this Example, it has been shown that within the limits of saturability of the system, large proportions of the radiolabeled VIP (up to 60%) were bound by lipid liposomes, indicating that partitioning into membranes could be a factor governing the availability of soluble peptide in extracellular fluids.

Second, binding of VIP by lipid particles or soluble lipids may stabilize the peptide to proteolysis and permit its delivery to distant target cells.

Third, partitioning of VIP into lipid bilayers may restrict the peptide into a specific conformation(s) and thus modify its interaction with membrane receptors.

Finally, local concentration of VIP within neuronal storage liposomes and at the site of release from nerve endings may be sufficient to directly modulate membrane function via changes in bilayer fluidity.

EXAMPLE 3

Liposomes containing mixtures of VIP and calmodulin were prepared in the manner set forth above in Examples 1. The measurement of hypotensive activity of the component mixtures set forth in Table 4 below were likewise done in manners set forth above. Arterial blood pressure readings shown below were taken five (5) minutes after the start of infusion of the component mixtures.

TABLE 4

|  | Mean Arterial Blood Preasure (mm Hg) | Heart Rate (min) |
|---|---|---|
| CONTROL | 111.7 | 324 |
| LIPO | 117.0 | 318 |
| 1 nmol VIP + LIPO | 53.3 | 408 |
| 1 nmol VIP + LIPO + 1 nmol calmodulin | 20.0 | 432 |

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the appended claims.

We claim:

1. A method of delivering a vasoactive intestinal polypeptide liposome product to a target tissue comprising the steps of;

encapsulating said vasoactive intestinal polypeptide (VIP) under conditions which result in VIP being expressed both on and in liposomes in a receptor active conformation to form a VIP liposome product; and administering a biologically effective amount of said VIP liposome product to said target tissue.

2. The method according to claim 1, wherein the liposomes contain cholesterol, phosphatidyl choline, and phosphatidyl glycerol.

3. The method according to claim 1 wherein said vasoactive intestinal polypeptide is complexed with lipid.

4. The method according to claim 1, wherein said receptor active conformation is helical.

5. The method according to claim 1, wherein said VIP liposome product is administered intravenously to treat hypertension.

6. The method according to claim 1, wherein said administration step includes the administration of a biologically effective amount of calmodulin along with the VIP liposome product.

7. The method of claim 6, wherein the administration step is performed with a preformed VIP-Calmodulin mixture expressed in and on liposomes.

8. A vasoactive intestinal polypeptide (VIP) liposome product wherein VIP is encapsulated in liposomes under conditions which result in VIP being expressed both on and in the liposomes in a receptor active conformation wherein the liposomes contain cholesterol, phosphatidyl choline, and phosphatidyl glycerol.

9. The vasoactive intestinal polypeptide liposome product according to claim 8, wherein said receptor active conformation results from complexing said vasoactive intestinal polypeptide with lipid.

10. The vasoactive intestinal polypeptide (VIP) liposome product according to claim 8, wherein said receptor active conformation is helical.

11. A vasoactive composition comprising a mixture of a biologically effective amount of a VIP and calmodulin liposome product wherein VIP and calmodulin are encapsulated in liposomes under conditions which result in VIP and calmodulin being expressed both on and in the liposomes wherein VIP is in a receptor active conformation.

12. A method of making a vasoactive intestinal polypeptide liposome product comprising the steps of;

forming said vasoactive intestinal Polypeptide (VIP) liposome product under conditions which result in VIP being encapsulated in liposomes under conditions which result in VIP being expressed both on and in the liposomes in a receptor active conformation.

13. The method according to claim 12, wherein said liposome contains cholesterol, phosphatidyl choline, and phosphatidyl glycerol.

14. The method according to claim 12, wherein said receptor active conformation is helical.

15. A method for controlling blood pressure in a mammal comprising the steps of;

administering an effective amount of the VIP liposome product according to claim 8 or the composition of claim 11 to said mammal.

16. A method of delivering a vasoactive intestinal polypeptide (VIP) family member liposome product to a target tissue comprising the steps of;

encapsulating said VIP family member under conditions which result in said VIP family member being expressed both on and in liposomes in a receptor active conformation to form a VIP family member liposome product, wherein said VIP family member is selected from the group consisting of vasoactive intestinal polypeptide, growth hormone releasing factor, pituitary adenylate cyclase activating peptide, secretin, peptide histidine methionine, helodermin, helospectin, and glucagon; and administering a biologically effective amount of said VIP family member liposome product to said target tissue.

17. The method according to claim 16, wherein said receptor active conformation is helical.

18. A vasoactive intestinal polypeptide (VIP) family member liposome product wherein said VIP family member is encapsulated in liposomes under conditions which result in said VIP family member being expressed both on and in the liposomes in a receptor active conformation wherein the liposomes contain cholesterol, phosphatidyl choline, and phosphatidyl glycerol; wherein said VIP family member is selected from the group consisting of vasoactive intestinal polypeptide, growth hormone releasing factor, pituitary adenylate cyclase activating peptide, secretin, peptide histidine methionine, helodermin, helospectin, and glucagon.

19. A method of making a vasoactive intestinal polypeptide (VIP) family member liposome product comprising the steps of;

forming said VIP family member liposome product under conditions which result in VIP family member being encapsulated in liposomes under conditions which result in VIP family member being expressed both on and in the liposomes in a receptor active conformation; wherein said VIP family member is selected from the group consisting of vasoactive intestinal polypeptide, growth hormone releasing factor, pituitary adenylate cyclase activating peptide, secretin, peptide histidine methionine, helodermin, helospectin, and glucagon.

20. The method according to claim 19, wherein said receptor active conformation is helical.

* * * * *